(12) United States Patent
Chandrasenan

(10) Patent No.: US 9,302,058 B2
(45) Date of Patent: Apr. 5, 2016

(54) INFUSION TUBING TRACING SYSTEM USING VIBRATION GENERATOR AND VIBRATION SENSOR

(71) Applicant: Curlin Medical Inc., East Aurora, NY (US)

(72) Inventor: Sreelal Chandrasenan, San Diego, CA (US)

(73) Assignee: CURLIN MEDICAL INC., East Aurora, NY (US)

( * ) Notice: Subject to any disclaimer, the term of this patent is extended or adjusted under 35 U.S.C. 154(b) by 167 days.

(21) Appl. No.: 13/833,305

(22) Filed: Mar. 15, 2013

(65) Prior Publication Data

US 2014/0276566 A1    Sep. 18, 2014

(51) Int. Cl.
| | |
|---|---|
| *A61M 5/142* | (2006.01) |
| *A61M 5/50* | (2006.01) |
| *G06Q 50/10* | (2012.01) |
| *A61M 5/14* | (2006.01) |
| *A61M 39/08* | (2006.01) |
| *G06F 19/00* | (2011.01) |

(52) U.S. Cl.
CPC ........... *A61M 5/5086* (2013.01); *A61M 5/1418* (2013.01); *A61M 39/08* (2013.01); *G06Q 50/10* (2013.01); *A61M 2039/087* (2013.01); *A61M 2205/18* (2013.01); *A61M 2205/332* (2013.01); *A61M 2205/502* (2013.01); *A61M 2205/6009* (2013.01); *G06F 19/3468* (2013.01)

(58) Field of Classification Search
CPC ............ G01M 7/00; G01M 7/02; G01H 1/00; G01H 17/00; G01N 29/045
See application file for complete search history.

(56) References Cited

U.S. PATENT DOCUMENTS

| | | | | |
|---|---|---|---|---|
| 3,855,487 | A | * | 12/1974 | Boisseau .......................... 310/80 |
| 4,846,792 | A | | 7/1989 | Bobo, Jr. et al. |
| 5,522,799 | A | | 6/1996 | Furukawa |
| 5,992,237 | A | * | 11/1999 | McCarty ................. F16C 19/52 702/56 |
| 2006/0265246 | A1 | * | 11/2006 | Hoag .................. A61M 5/1413 705/2 |
| 2007/0083153 | A1 | | 4/2007 | Haar |
| 2008/0098798 | A1 | | 5/2008 | Riley |
| 2011/0264045 | A1 | * | 10/2011 | Thompson ............ A61M 5/142 604/151 |

OTHER PUBLICATIONS

WIPO, International Preliminary Report on Patentability, issued Sep. 15, 2015 in International Application No. PCT/US2014/025157.

* cited by examiner

*Primary Examiner* — Emily Schmidt
*Assistant Examiner* — William Frehe
(74) *Attorney, Agent, or Firm* — Hodgson Russ LLP

(57) ABSTRACT

A system for tracing tubing which forms a conduit from a source of infusion liquid to a patient by way of an infusion pump has a vibration generator manually operable by a user to generate vibrations at an origin location along the tubing, wherein the vibrations are propagated by the tubing and have a vibration signature. A vibration sensor arranged at a destination location along the tubing receives the vibrations and generates a digital vibration signal. Signal processing circuitry connected to the vibration sensor processes and evaluates the digital vibration signal to determine a trace status of the tubing between the vibration generator and the vibration sensor. An indicator connected to the signal processing circuitry provides an indication of the determined trace status. Trace status possibilities include clear, cross-over, and null. A likely number of cross-overs may also be indicated.

15 Claims, 3 Drawing Sheets

INFUSION TUBING TRACING SYSTEM USING VIBRATION GENERATOR AND VIBRATION SENSOR

FIELD OF THE INVENTION

The present invention relates generally to infusion pumps for delivering medication and nutritional fluids to a patient, and more particularly to a system for tracing infusion tubing lines to confirm intended connections to the proper fluid source, infusion pump, and/or patient.

BACKGROUND OF THE INVENTION

When multiple infusion pumps are connected to a patient or multichannel infusion pumps are used, it becomes difficult to trace the right tubing line for priming, fluid supply management, locating and correcting occlusions and air-in-line, making set-up connections, and making disconnections.

Current infusion pumps do not have an automated way of tracing the lines. According to current clinical practice, before tubing is connected or reconnected to a patient, a staff clinician is required to completely trace the infusion tubing line from the patient through the pump to the source of fluid for verification. To assist manual tracing, sometimes the infusion tubing lines are manually labeled. The current solution of manually tracing tubing lines is not very efficient and it can introduce errors that could potentially harm the patient. Manual line tracing delays therapy and takes a lot of valuable time from the clinician. More importantly, potential connection errors may occur and have potentially hazardous consequences to the patient. Some of the critical errors are tubing misconnections and air embolism.

U.S. Patent Application Publication No. 2011/0264045 addresses the problem of tracing a tubing line from the pump to the patient by providing a sensor in the pump near a downstream connection receiving an end of the tubing. The clinician squeezes the tubing anywhere along its length between the pump and the patient, and the pressure pulse generated by the squeezing action is detected by the sensor, which triggers an alarm at the pump. While this system represents progress, it has its shortcomings. For example, it does not provide for tracing between the fluid source and the pump. Also, where two or more lines are crossed and touch one another, there is no indication of such a cross-over condition and the other lines involved are not identified to the clinician.

There is a need for a more robust automatic tracing system.

SUMMARY OF THE INVENTION

The present invention provides a tubing line tracing system that uses vibration generators, vibration sensors, and audio and/or visual indicators to perform line traces and inform the clinician of a trace status. It also provides a system capable of detecting line cross-overs where two different tubing lines touch one another and identifying to the clinician which lines are involved in the cross-over. The present invention helps clinicians organize the infusion tubing lines, and also supports manual tracing by the clinician.

In an aspect of the invention, a system for tracing tubing which forms a conduit from a source of infusion liquid to a patient by way of an infusion pump is provided. The system comprises a vibration generator manually operable by a user to generate vibrations at an origin location along the tubing, wherein the vibrations are propagated by the tubing and have a vibration signature. The system also comprises a vibration sensor arranged at a destination location along the tubing for receiving the propagated vibrations and generating a digital vibration signal representative of the received vibrations. Signal processing circuitry is connected to the vibration sensor and is configured to process and evaluate the digital vibration signal to determine a trace status of the tubing between the vibration generator and the vibration sensor. The system further comprises an indicator connected to the signal processing circuitry. The indicator is configured to provide an audible or visual indication of the determined trace status. The trace status may be selected from a status group consisting of a clear trace status, a cross-over trace status indicating touching tubing lines, and a null trace status. One of the vibration generator and the vibration sensor may be removably attachable to the tubing at a desired location, and the other of the vibration generator and the vibration sensor may be part of the infusion pump.

In another aspect of the present invention, a system is provided for tracing first tubing which forms a conduit from a first source of infusion liquid to a patient by way of a first infusion pump and second tubing which forms a conduit from a second source of infusion liquid to the patient or to another patient by way of a second infusion pump. The system comprises a vibration generator manually operable by a user to generate vibrations at an origin location along the first tubing, wherein the vibrations are propagated by the first tubing and have a vibration signature. The system further comprises a vibration sensor arranged at a location along the second tubing, wherein the vibrations are also propagated by the second tubing if there is a cross-over between of the first tubing with the second tubing. The vibration sensor receives the vibrations propagated by the second tubing and generates a digital vibration signal representative of the received vibrations. An indicator connected to the vibration sensor is configured to provide an audible or visual indication in response to the digital vibration signal. In this way, a cross-over culprit can be readily identified.

The present invention further encompasses a method of tracing tubing which forms a conduit from a source of infusion liquid to a patient by way of an infusion pump. The method comprises arranging a vibration generator in engagement with the tubing at an origin location along the tubing, and arranging a vibration sensor in engagement with the tubing at a destination location along the tubing. The method further comprises activating the vibration generator to cause the vibration generator to generate vibrations at the origin location, wherein the vibrations are propagated by the tubing and have a vibration signature, and receiving the propagated vibrations at the vibration sensor. The method additionally comprises generating a digital vibration signal representative of the received vibrations, and determining a trace status of the first tubing between the vibration generator and the vibration sensor based on the digital vibration signal.

BRIEF DESCRIPTION OF THE DRAWING VIEWS

The invention will be described in detail below with reference to the accompanying drawing figures, in which.

DETAILED DESCRIPTION OF THE INVENTION

Figure 1:
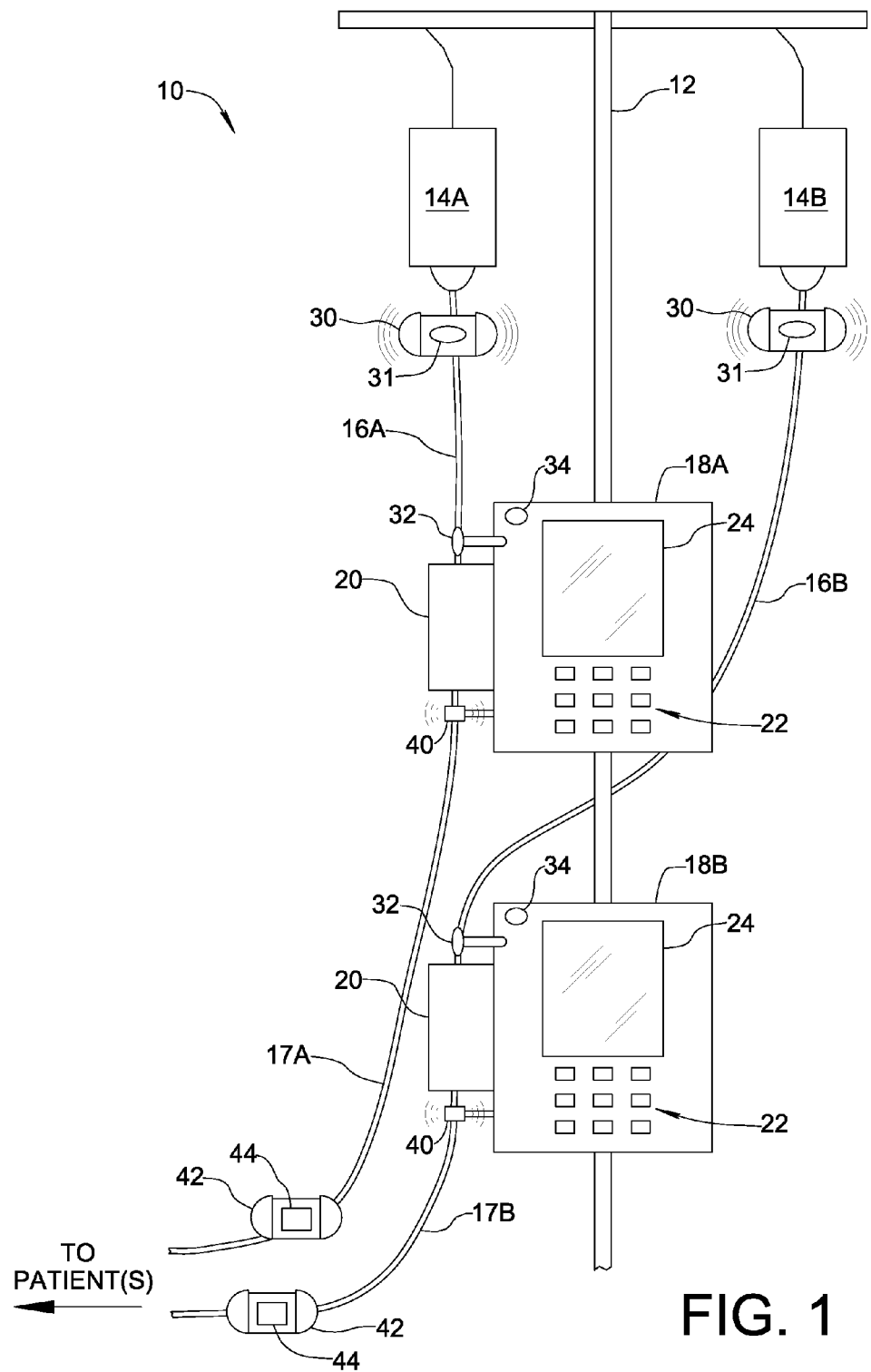
FIG. 1 is a schematic illustration of an infusion pump system embodying the present invention.

FIG. 1 schematically illustrates a tracing system 10 configured in accordance with a first embodiment of the present invention. Tracing system 10 is installed in a health care facility environment in which patients are treated by infusing fluids into the body using one or more infusion pumps. FIG. 1 shows an infusion pole 12, e.g. an IV pole associated with intravenous infusions, supporting a first source of infusion liquid 14A and a second source of infusion liquid 14B. First source 14A is connected to a first infusion pump 18A by a tubing segment 16A providing flow input to pumping mechanism 20 of pump 18B. By way of non-limiting example, pumping mechanism 20 may be a peristaltic pumping mechanism. Tubing line 16A typically connects to an input port on pump 18A for communication with a short tubing segment within the pump that specifically intended for the type of pumping mechanism being used. For example, in a peristaltic pump, the material of the internal tubing segment may be specially chosen for performance under peristaltic pumping action compressing the tubing. Output flow from pump 18A is carried by tubing line 17A to a patient. As mentioned, tubing lines 16A and 17A are typically connected via an internal shorter tubing segment within the pumping mechanism, however tubing lines 16A and 17A may be part of one continuous tubing line arranged to extend through the pumping mechanism. Thus, tubing lines 16A and 17A form a conduit from source 14A to a patient, either with the help of an additional tubing segment or flow channel within pump mechanism 20 or on their own. In addition to pumping mechanism 20, infusion pump 18A includes a keypad 22 and a display 24 connected to internal electronics and memory for programming and controlling the infusion pump. As will be understood, the second infusion pump 18B is part of a similar setup that also includes the second fluid source 14B, a tubing line 16B from second source 14B to second pump 18B, and a tubing line 17B from second pump 18B to a patient. Tubing lines 17A and 17B may be connected to the same patient, or to two different patients. The system configuration described thus far is known in the art of infusion treatment.

In accordance with an embodiment of the present invention, a vibration generator 30 is removably attached to tubing line 16A and includes an activation switch 31. For sake of illustration, vibration generator 30 is attached to tubing line 16A at an origin location proximate first source 14A, however vibration generator 30 can be located anywhere along the tubing line depending on what portion of the line the clinician seeks to trace. A vibration sensor 32 is arranged on pump 18A and is in contact with tubing line 16A at a destination location near the input connection of tubing line 16A with the pump. Vibration sensor 32 is connected to the pump's internal electronics. A trace indicator 34 is provided on pump 18A and is responsive to vibration sensor 32, as will be described below, to provide a trace status indication to the clinician. Trace indicator 34 may be a visual device such an LED array, a display (e.g. an LCD), or an audio device, or a combination of visual and audio devices. In an embodiment of the present invention, pump display 24 may be used as the trace indicator.

Vibration generator 30 is manually operable by the clinician using activation switch 31 to generate vibrations at the origin location. The vibrations are propagated by the tubing and have a vibration signature. For example, the signature may be defined by predetermined frequency and amplitude characteristics or modulation of the vibrations. Vibration sensor 32 receives the propagated vibrations at the destination location and generates a digital vibration signal representative of the received vibrations.

Figure 3:
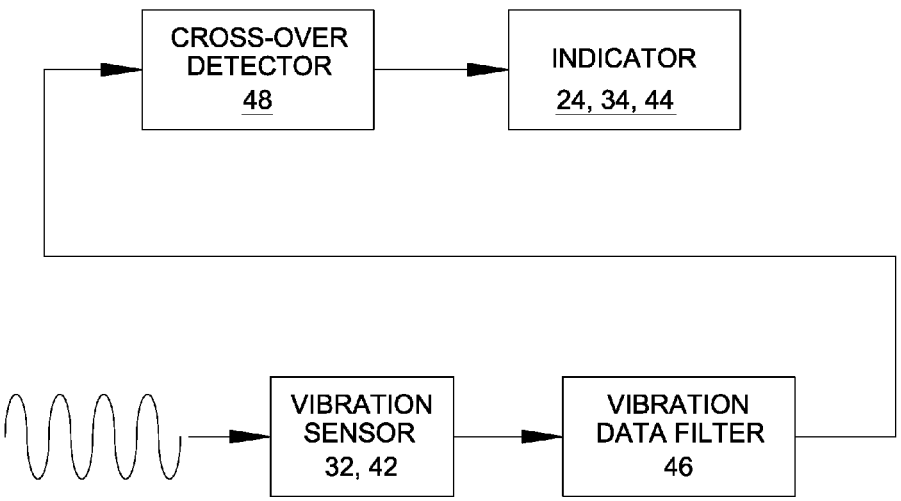
FIG. 3 is an block diagram illustrating signal processing circuitry in accordance with an embodiment of the present invention.

Reference is now made to FIG. 3. The digital vibration signal from vibration sensor 32 is processed by signal processing circuitry to determine a trace status of tubing line 16A between vibration generator 30 and vibration sensor 32. In an embodiment of the present invention, the determined trace status is selected from a status group consisting of a clear trace status corresponding to a successful trace wherein a vibration signature of the received vibrations corresponds to an expected vibration signature, a cross-over trace status indicating at least one cross-over exists, and a null trace status indicating that the trace was unsuccessful (i.e. the vibrations were not received at the destination location). The cross-over trace status may include a likely number of cross-overs.

In the present embodiment, the digital vibration signal is filtered by a vibration data filter 46 to remove noise from the sampled signal. The filtered vibration signal is sent to a crossover detector 48 configured to analyze the vibration signal with respect to the vibration signature and possible cross-over condition(s). The signature analysis approach will depend on the nature of the vibration signature. Performing frequency and peak amplitude measurement methods or averaging amplitudes for selected frequencies and for selected signal portions are approaches that may be used for vibration signature analysis. Cross-over conditions can be determined by detecting a phase shift or by detecting various harmonics. Another approach to cross-over detection is to integrate the signal values to compute the RMS velocity or displacement over frequency and compare cross-over and non-cross over values to establish cross-over detection parameters. Cross-over detector 48 may be configured to simply determine whether or not a cross-over exits, or it may be configured to determine a likely number of cross-overs existing along the traced tubing.

Figures 4A, 4B, 4C:
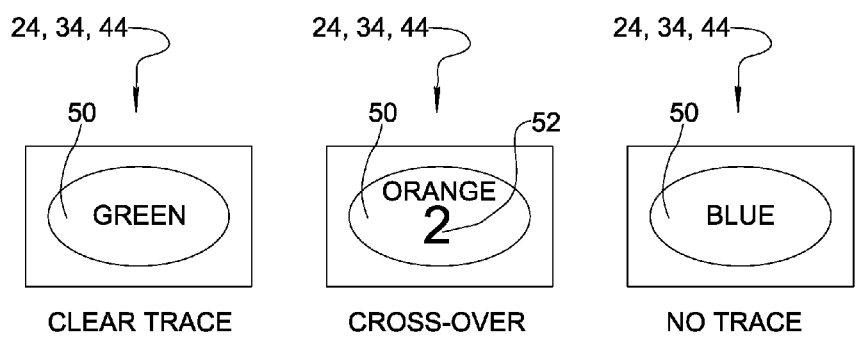
FIGS. 4A-4C are schematic illustrations of various trace status indications in accordance with an embodiment of the present invention.

The trace status information is forwarded by cross-over detector 48 to indicator 34 (or display 24) for providing an indication of the determined trace status. FIGS. 4A-4C give illustrative examples of possible visual indications of trace status. FIG. 4A shows a clear trace status indication using a color-coded icon 50. In the example of FIG. 4A, the color green is used to indicate a clear trace status. FIG. 4B shows a cross-over status indication wherein color-coded icon 50 is rendered orange to indicate cross-over status, and a character display 52 is provided to indicate a likely number of cross-overs as determined by cross-over detector 48. FIG. 4C shows a cross-over status indication wherein color-coded icon 50 is rendered blue to indicate a null trace status (no successful trace). Of course, different colors and icon shapes may be used without straying from the present invention.

Attention is directed again to FIG. 1. In the description above, vibration generator 30 is removably attached to the infusion tubing line and vibration sensor 32 is part of pump 18A. However, this arrangement may be reversed. A vibration generator 40 is provided on pump 18A to introduce vibrations at an origin location adjacent a downstream end of pumping mechanism 20, and a vibration sensor 42 is removably attached to tubing line 17A at a destination location between the pump and the patient. Vibration generator 40 may be activated by pressing one key or a combination of keys in keypad 22. Alternatively, a dedicated activation switch may be provided on the pump for activating vibration generator 40. Vibration sensor 42 includes an on-board indicator 44 and internal signal processing circuitry connected to indicator 44. Again, a similar arrangement is associated with pump 18B.

The mechanism for removably attaching vibration generator 30 and vibration sensor 42 to a tubing line at a selected location is subject to wide variation. A spring-loaded clip or pinching mechanism may be used, as may any suitable attachment means, including friction fit with no spring loading. The attachment mechanism should be chosen so as not to interfere with vibrations being generated or sensed, or with flow through the tubing.

As will be understood, if line 16A contacts line 16B and a line trace is initiated from vibration generator 30 on line 16A, vibrations will be propagated not only to vibration sensor 32 on first pump 18A, but also to vibration sensor 32 on second pump 18B. As described above, a cross-over trace status will be determined for line 16A. In accordance with the present invention, indicator 34 on second pump 18B may indicate that line 16B is in contact with line 16A in the cross-over. Indicator 34 on second pump 18B may indicate whether or not the vibration signature of the received vibrations corresponds to an expected vibration signature associated with vibration sensor 32 on second pump 18B, so the clinician knows that a "foreign" trace vibration was received by second pump 18B. Similar logic may be provided in removably attachable sensors 42. Thus, the cross-over may be located quickly and the tubing lines organized to remove the cross-over.

Figure 2:
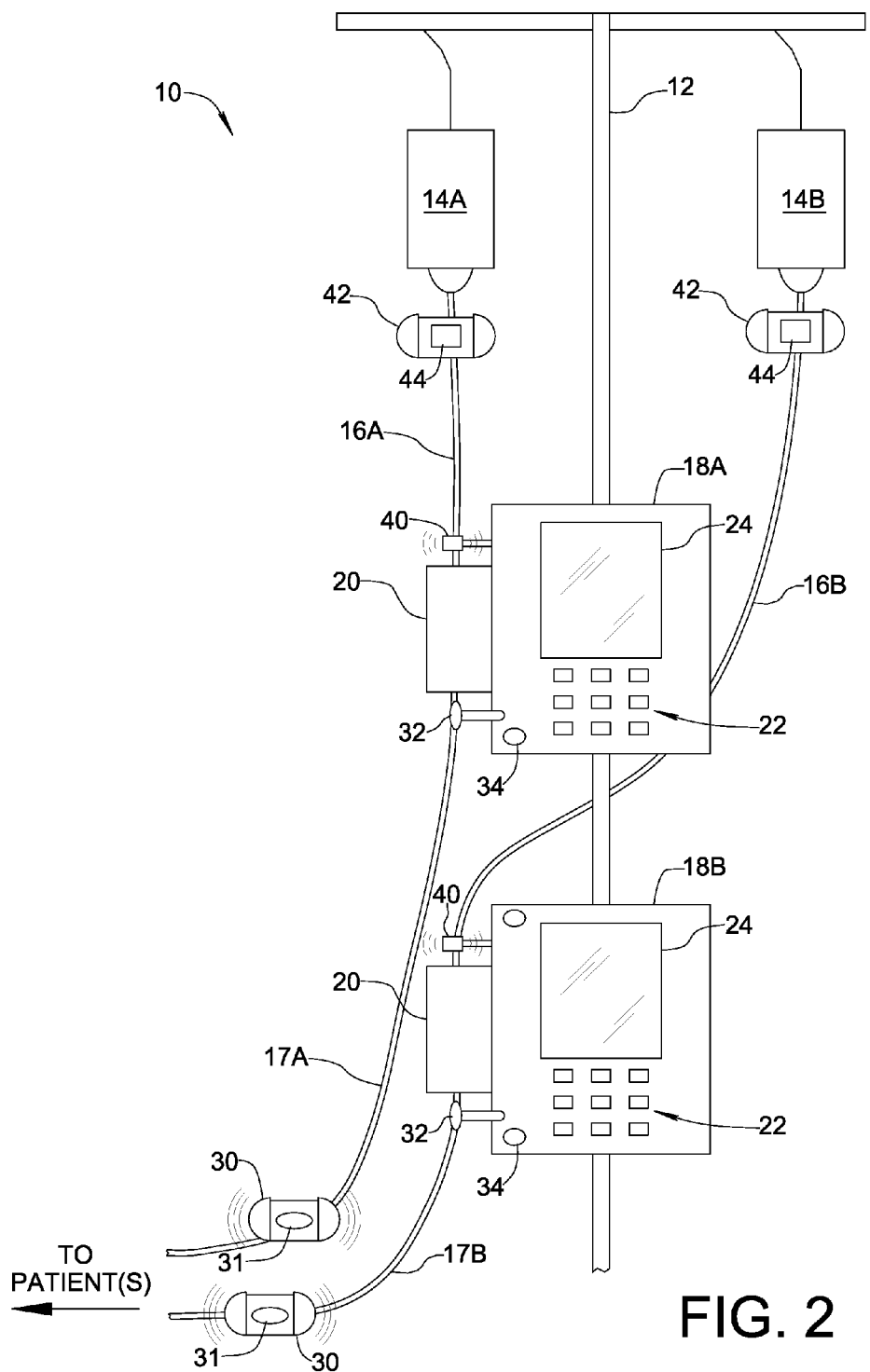
FIG. 2 is a schematic illustration of another infusion pump system embodying the present invention.

FIG. 2 shows system 10 in an alternate configuration wherein the pump vibration generator 40 sends vibrations to a vibration sensor 42 removably attached to tubing line 16A between first source 14A and first pump 18A. FIG. 2 also shows a vibration generator 30 removably attached to tubing line 17A between first pump 18A and the patient for sending vibrations to vibration sensor 32 on first pump 18A. Second pump 18B in FIG. 2 is part of a similar configuration. Of course, other configurations are possible. For example, a removably attachable vibration generator 30 and a removably attachable vibration sensor 42 may be attached at different locations along the same infusion line for communication with one another to trace the tubing line between them. In another example, the pump 18A or 18B may have two vibration generators 40, one upstream from pumping mechanism 20 and one downstream from pumping mechanism 20, for communication with corresponding vibrations sensors 42 located between the source and the pump and between the pump and the patient, respectively. In yet another example, the pump 18A or 18B may have two vibration sensors 32, one upstream from pumping mechanism 20 and one downstream from pumping mechanism 20, for receiving vibrations from corresponding vibrations generators 30 located between the source and the pump and between the pump and the patient, respectively.

Embodiments of the present invention are described in detail herein, however those skilled in the art will realize that modifications may be made. Such modifications do not stray from the spirit and scope of the invention as defined by the appended claims.

PARTS LIST

10 Tracing system for infusion tubing
12 Infusion pole
14A First source of infusion liquid
14B Second source of infusion liquid
16A Tubing between first liquid source and first pump
16B Tubing between second liquid source and second pump
17A Tubing between first pump and patient
17B Tubing between second pump and patient (or another patient)
18A First infusion pump
18B Second infusion pump
20 Pumping mechanism
22 Keypad
24 Display
30 Vibration generator (removably attachable to tubing)
31 Activation switch for vibration generator
32 Vibration sensor (on pump)
34 Indicator (on pump)
40 Vibration generator (on pump)
42 Vibration sensor (removably attachable to tubing)
44 Indicator (on vibration sensor)
46 Vibration data filter
48 Cross-over detector
50 Indicator color icon
52 Indicator character display

What is claimed is:

1. A system for tracing tubing which forms a conduit from a source of infusion liquid to a patient by way of an infusion pump, the system comprising:
   a vibration generator manually operable by a user to generate vibrations at an origin location along the tubing, wherein the vibrations are propagated by the tubing and have a vibration signature;
   a vibration sensor arranged at a destination location along the tubing for receiving the propagated vibrations and generating a digital vibration signal representative of the received vibrations;
   signal processing circuitry connected to the vibration sensor, wherein the signal processing circuitry is configured to process and evaluate the digital vibration signal to determine a trace status of the tubing between the vibration generator and the vibration sensor, wherein the signal processing circuitry determines a cross-over trace status when the tubing is touched by other tubing; and
   an indicator connected to the signal processing circuitry, wherein the indicator is configured to provide an audible or visual indication of the determined trace status.

2. The system according to claim 1, wherein one of the vibration generator and the vibration sensor is removably attachable to the tubing at a selected location along the tubing, and the other of the vibration generator and the vibration sensor is part of the pump.

3. The system according to claim 2, wherein the vibration generator is removably attachable to the tubing at a selected origin location along the tubing, and the vibration sensor is part of the pump.

4. The system according to claim 3, wherein the indicator and the signal processing circuitry are part of the pump.

5. The system according to claim 3, wherein the selected origin location is between the source of infusion liquid and the pump.

6. The system according to claim 3, wherein the selected origin location is between the patient and the pump.

7. The system according to claim 2, wherein the vibration generator is part of the pump, and the vibration sensor is removably attachable to the tubing at a selected destination location along the tubing.

8. The system according to claim 7, wherein the indicator and the signal processing circuitry are housed with the vibration sensor for removable attachment to the tubing.

9. The system according to claim 7, wherein the selected destination location is between the pump and the patient.

10. The system according to claim 7, wherein the selected destination location is between the pump and the source of infusion liquid.

11. The system according to claim 1, wherein the vibration generator is removably attachable to the tubing at a selected origin location along the tubing, and the vibration sensor is removably attachable to the tubing at a selected destination location along the tubing.

12. The system according to claim 1, wherein the determined trace status is selected from a status group consisting of a clear trace status, the cross-over trace status, and a null trace status.

13. A system for tracing tubing which forms a conduit from a source of infusion liquid to a patient by way of an infusion pump, the system comprising:
- a vibration generator manually operable by a user to generate vibrations at an origin location along the tubing, wherein the vibrations are propagated by the tubing and have a vibration signature;
- a vibration sensor arranged at a destination location along the tubing for receiving the propagated vibrations and generating a digital vibration signal representative of the received vibrations;
- signal processing circuitry connected to the vibration sensor, wherein the signal processing circuitry is configured to process and evaluate the digital vibration signal to determine a trace status of the tubing between the vibration generator and the vibration sensor; and
- an indicator connected to the signal processing circuitry, wherein the indicator is configured to provide an audible or visual indication of the determined trace status;
- wherein the determined trace status is selected from a status group consisting of a clear trace status, a cross-over trace status, and a null trace status; and
- wherein the signal processing circuitry is configured to process and evaluate the digital vibration signal to determine a likely number of cross-overs as part of the cross-over trace status.

14. A system for tracing first tubing which forms a conduit from a first source of infusion liquid to a patient by way of a first infusion pump and second tubing which forms a conduit from a second source of infusion liquid to the patient or to another patient by way of a second infusion pump, the system comprising:
- a first vibration generator manually operable by a user to generate first vibrations at an origin location along the first tubing, wherein the first vibrations are propagated by the first tubing and have a first vibration signature;
- a second vibration generator manually operable by a user to generate second vibrations at an origin location along the second tubing, wherein the second vibrations are propagated by the second tubing and have a second vibration signature;
- a vibration sensor arranged at a location along the second tubing, wherein the first vibrations are also propagated by the second tubing if there is a cross-over of the first tubing with the second tubing such that the first tubing touches the second tubing, the vibration sensor receiving the first and second vibrations propagated by the second tubing and generating a digital vibration signal representative of the received vibrations;
- signal processing circuitry connected to the vibration sensor, wherein the signal processing circuitry is configured to process and evaluate the digital vibration signal to determine whether the received vibrations have a vibration signature corresponding to the second vibration signature; and
- an indicator connected to the vibration sensor, the indicator being configured to provide an audible or visual indication of the cross-over in response to the digital vibration signal.

15. The system according to claim 14, wherein the indication informs a user as to whether or not the vibration signature of the received vibrations corresponds to the second vibration signature.

* * * * *